US006410752B1

(12) United States Patent
Kim et al.

(10) Patent No.: US 6,410,752 B1
(45) Date of Patent: Jun. 25, 2002

(54) TOCOPHEROL DERIVATIVES AND METHOD FOR PREPARATION THEREOF

(75) Inventors: Kil Joong Kim, Suwon-shi; Duck Hee Kim, Seoul; Ho Sik Rho, Euiwang-shi; Jae Won You, Seoul; Chun Ja Nam, Suwon-shi; Jong Eoun Hong, Seoul; Hak Hee Kang, Seongnam-shi; Ih Seob Chang, Yongin-shi, all of (KR)

(73) Assignee: Pacific Corporation, Seoul (KR)

( * ) Notice: Subject to any disclaimer, the term of this patent is extended or adjusted under 35 U.S.C. 154(b) by 0 days.

(21) Appl. No.: 09/756,179

(22) Filed: Jan. 9, 2001

(30) Foreign Application Priority Data

Aug. 29, 2000 (KR) ........................................ 2000-50330

(51) Int. Cl.[7] .......................... C07F 9/06; C07D 311/72

(52) U.S. Cl. ........................ 549/220; 549/412; 549/413

(58) Field of Search ................................ 549/220, 412, 549/413

(56) References Cited

U.S. PATENT DOCUMENTS 4,564,686 A 1/1986 Ogata ......................... 549/220

*Primary Examiner*—T. A. Solola
(74) *Attorney, Agent, or Firm*—Sughrue Mion, PLLC

(57) ABSTRACT

An object of the present invention is to provide the tocopherol derivatives represented by the following formula (I), and their salts:

(1)

$$^{+}H_3N\text{–}CH_2CH_2CH_2\text{–}O\text{–}P(=O)(O^-)\text{–}O\text{–}[\text{chroman ring with } R_1, R_2, R_3, CH_3]\text{–}(CH_2CH_2\text{–}A)_3\text{–}CH_3$$

Wherein, $R_1$, $R_2$ and $R_3$ are H or methyl group, and at least one positions selected from group consisting of the $R_1$, $R_2$ and $R_3$ positions are methyl group; and, A is $CH_2$—$CH(CH_3)$— or $CH{=}C(CH_3)$—

The other object of the present invention is to provide a method for preparing the above tocopherol derivatives. The tocopherol derivatives is prepared by reacting tocopherol with phosphorous oxychloride in an equivalent ratio of 1:1~1.3, in presence of an organic base, in an organic solvent; reacting the tocopherol dichlorophosphate produced by the above reaction with 3-aminopropanol in presence of an organic base, in an organic solvent; and, hydrolyzing the above products.

The tocopherol derivatives according to the present invention can be hydrolyzed by biological enzymes in a living body to produce tocopherol and 3-aminopropane phosphate. And they can induce physiological activities including recovery of injured skin, prevention from aging of biomembrane, etc. Also, the tocopherol derivatives according to the present invention have improved stability, safety to skin and anti-oxidant effect superior to preceding tocopherol and its derivatives.

4 Claims, 1 Drawing Sheet

TOCOPHEROL DERIVATIVES AND METHOD FOR PREPARATION THEREOF

BACKGROUND OF THE INVENTION

1. Field of the Invention

The present invention is related to tocopherol derivatives and their salts, and to method for preparation thereof.

2. Description of the Related Arts

Cosmetics have the purpose of neatening and beautifying skin and hair, and giving nutrients and health to them. In particular, much research has been devoted recently to inhibiting fine wrinkles on skin through the activation of dermal cells. As a result, many materials have been developed. For example, it was reported that materials including vitamins such as retinol and ascorbic acid, proteins and flavonoid extracted from various plants and animals, amino acids, epidermal growth factor and α-hydroxyl acid are effective in inhibiting fine wrinkles on the skin. Such materials are applied to cosmetics and the like. However, most of traditional materials effective on fine wrinkles of skin have defects including low stability of the effective ingredient and the like.

Further, it was reported that tocopherol, one of liposoluble-type vitamins, has bioactive functions including a protective function against activity of free radicals which are harmful to human body, promotion of cell growth, and induction of collagen biosynthesis, anti-allergy effects and anti-inflammatory effects. Therefore, tocopherol has also been used as a cosmetic source because of its bioactivities. However, the unstable, liposoluble and water-insoluble properties of tocopherol have limited the uses of tocopherol as a cosmetic source.

Recently, many tocopherol derivatives have been developed in order to improve its stability. For example, U.S. Pat. No. 4,564,686 disclosed that compounds produced by phosphatic esterification between tocopherol and ascorbic acid could improve the stability of tocopherol. However, the traditionally known tocopherol derivatives could improve only the stability of tocopherol. And they were materials combined simply through the esterification between tocopherol and compounds with similar physiological activities. However, tocopherol derivatives introduced with compounds with other physiological activities have still not been developed.

Under these circumstances, the present inventors have conducted much research to prepare tocopherol derivatives into which compounds with other physiological activities may be introduced, so that other bioactivities and improved stability of tocopherol can be obtained thereby. As a result, it was found that the tocopherol derivatives introduced with 3-aminopropane phosphate could be hydrolyzed through biological enzymes in a living body, and the tocopherol-hydrolyzed products, tocopherol and 3-aminopropane phosphate, can perform different physiological activitives. In addition, these tocopherol derivatives have both hydrophilic and hydrophobic groups, thus show improved stability in aqueous mediums. And these tocopherol derivatives also show a much more improved anti-oxidative effect than tocopherol.

SUMMARY OF THE INVENTION

Thus, an object of the present invention is to provide the tocopherol derivatives represented by the following formula (I), and their salts:

(1)

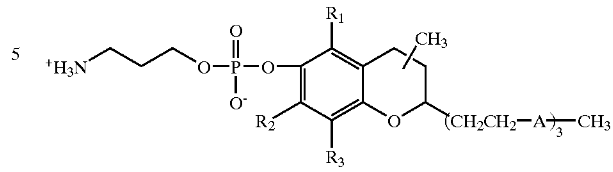

Wherein, $R_1$, $R_2$ and $R_3$ are H or methyl group, and at least one positions selected from group consisting of the $R_1$, $R_2$ and $R_3$ positions are methyl group; and, A is $CH_2$—$CH(CH_3)$— or $CH{=}C(CH_3)$—

The other object of the present invention is to provide a method for preparing the above tocopherol derivatives. The tocopherol derivatives is prepared by reacting tocopherol with phosphorous oxychloride in an equivalent ratio of 1:1~1.3, in presence of an organic base, in an organic solvent; reacting the tocopherol dichlorophosphate produced by the above reaction with 3-aminopropanol in presence of an organic base, in an organic solvent; and, hydrolyzing the above products.

The tocopherol derivatives according to the present invention can be hydrolyzed by biological enzymes in a living body to produce tocopherol and 3-aminopropane phosphate. And they can induce physiological activities including recovery of injured skin, prevention from aging of biomembrane, etc. Also, the tocopherol derivatives according to the present invention have improved stability, safety to skin and anti-oxidant effect superior to preceding tocopherol and its derivatives.

DETAILED DESCRIPTION OF THE INVENTION

Figure 1:
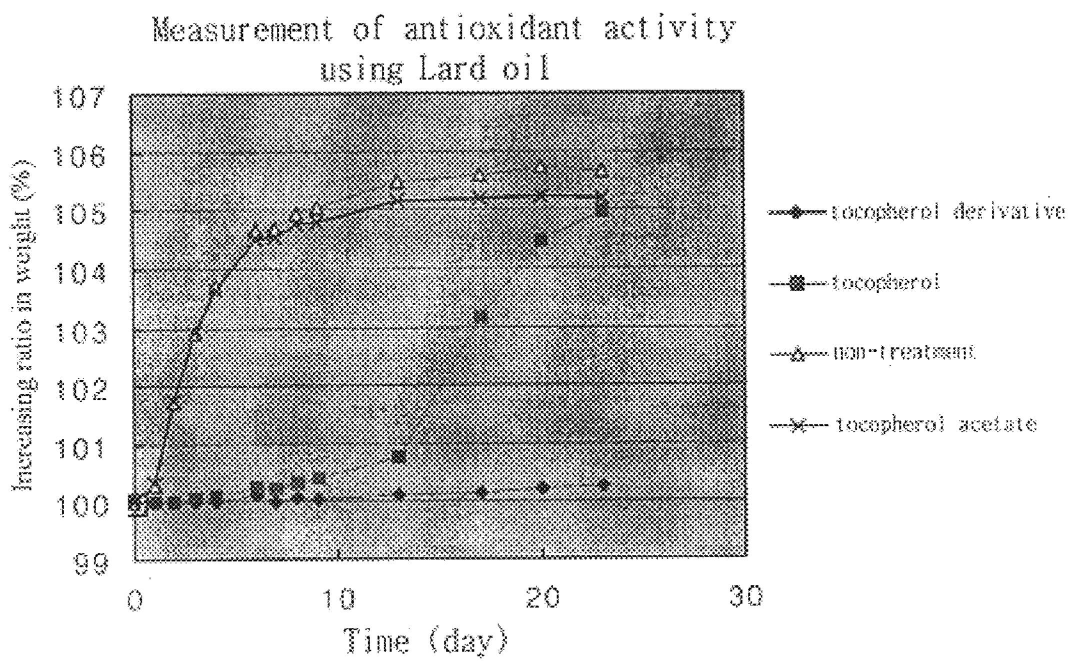
FIG. 1. Measurement of antioxidant activity using Lard oil.
Figure 2:
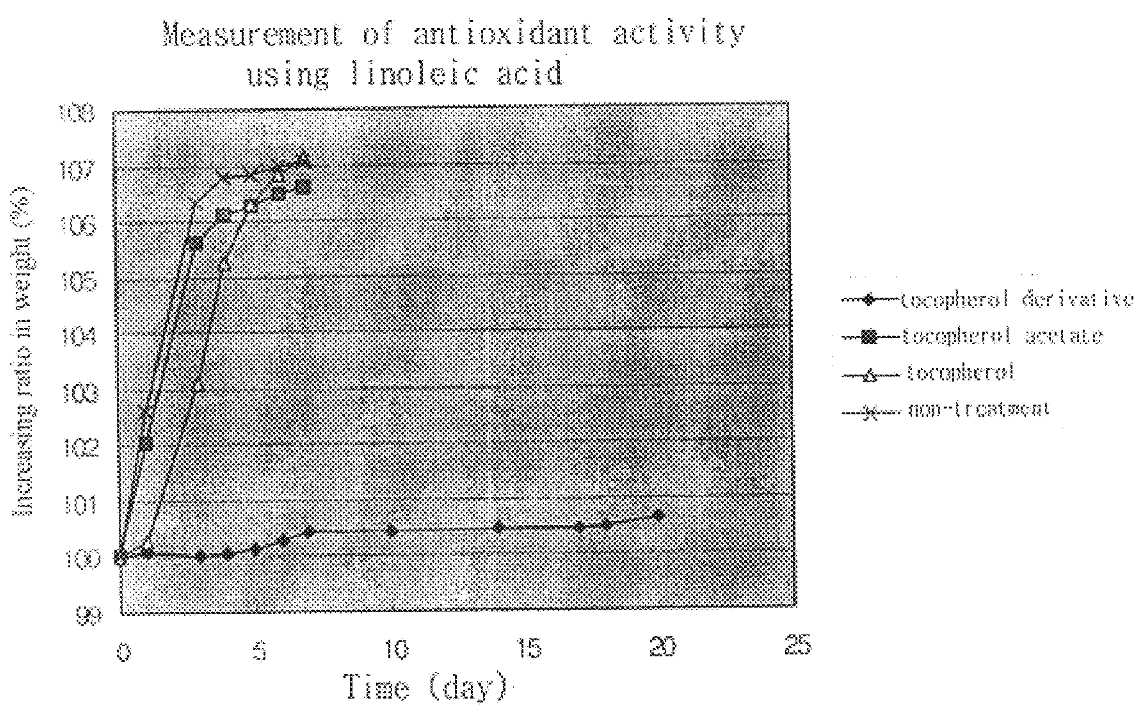
FIG. 2. Measurement of antioxidant activity using linoleic acid.

The tocopherol derivatives according to the invention are materials which can be hydrolyzed by biological enzymes, thereby can release tocopherol and 3-aminopropane phosphate. They have effects including prevention of biolipids oxidation and promotion of collagen biosynthesis, and they are also safe to skin and can provide improved effects such as an increase in elasticity of skin and prevention of skin aging. Moreover, the tocopherol derivatives according to the present invention have excellent anti-oxidant effect and stability in both water and lipid media by possessing both hydrophilic and lipophilic groups. Therefore, the tocopherol derivatives of the invention may have various usages such as cosmetic composition.

The tocopherol derivatives according to the present invention are represented by the following formula (I):

(1)

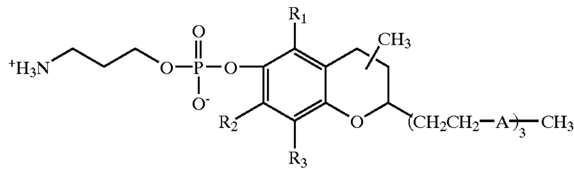

Wherein, $R_1$, $R_2$ and $R_3$ are H or methyl group, and at least one positions selected from group consisting of the $R_1$, $R_2$ and $R_3$ positions are methyl group; and, A is $CH_2$—$CH(CH_3)$— or $CH{=}C(CH_3)$—

The method for preparing the tocopherol derivatives of the above general formula (I) comprises the following steps:

(A) reacting tocopherol with phosphorous oxychloride at a temperature of −10~50° C. in an equivalent ratio of 1:1~1.3, in presence of an organic base, in an organic solvent to produce tocopherol dicholophosphate;

(B) reacting the tocopherol dichlorophosphate produced by the above (A) step with 3-aminopropanol in presence of an organic base, in an organic solvent to produce 2-tocopherol-tetrahydro-2H-1,3,2-oxazaphosphorin P-Oxide;

(C) filtering the solution containing 2-tocopherol-tetrahydro-2H-1,3,2-oxazaphosphorin P-Oxide produced by the step (B), and then adjusting pH of filtrate to 1~5 and hydrolyzing the results at a temperature of 5~100° C., for 1~10 hours; and, (D) extracting tocopherol derivatives with an organic solvent and purifying them.

The method may be illustrated by a following Reaction Schema (I):

(A)

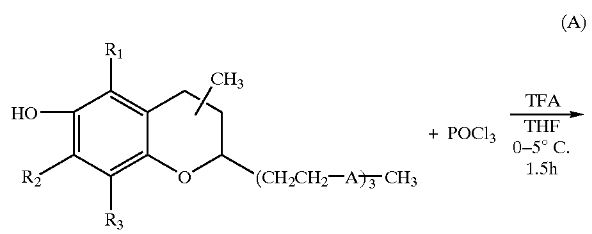

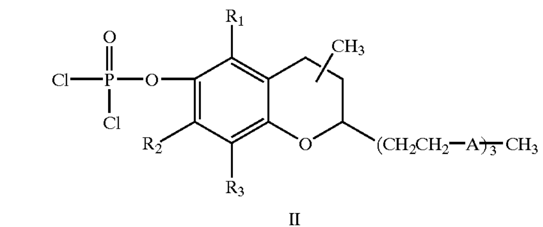

II (B)

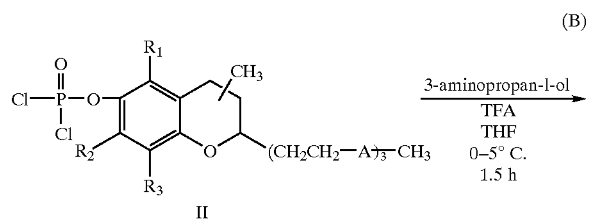

II

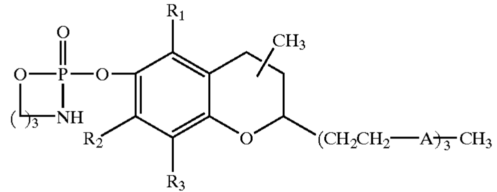

III (C)

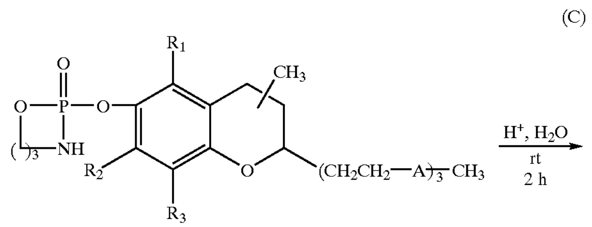

III

-continued

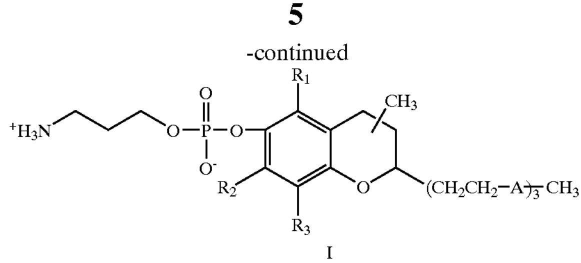

In detail, the method for preparing tocopherol derivatives represented by Reaction Schema (I) is explained as follows.

(A) reacting tocopherol with phosphorus oxychloride, stirring at a temperature of −10~50° C. in an organic solvent, in the presence of organic base, for 1~3 hours to produce tocopherol diclorophosphate;

In step (A), it is preferable that the reaction of tocopherol with phosphorus oxychloride is carried out in an equivalent ratio 1:1~1.3. In case that this ratio is lower than 1:1, the object product cannot be obtained. While, in case that the ratio is higher than 1:1.3, excessive by-products as well as the object product are obtained.

In this step, an intermediate complex of tocopherol and phosphorus oxychloride is produced with a yield of 95% or more, and ditocopherol phosphate as a by-product, 2:1 complex of tocopherol and phosphorus oxychloride is produced with a yield of 3% or less. However, ditocopherol phosphate may be removed simply by step (B) and (C), and through a purification step, triethylamine hydrochloride salt is removed though filtration of the reaction solution.

The organic base employed in this step may include, but not limited thereto, pyridine and triethylamine. Among them, triethylamine may be preferable.

Further, the organic solvent employed in this step may include, but not limited thereto, dichloromethane, tetrahydrofuran, ethyl acetate, acetonitrile, chloroform, ethyl ether and other inert solvents. Among them, tetrahydrofuran may be preferable.

In the meantime, at a temperature of higher than 50° C., two or more equivalent ratio of tocopherol may react with one equivalent ratio of phosphorus oxychloride, resulting in production of by-product thereby. While, at a lower temperature than −10° C., the reaction may proceed slowly. Thus, it is preferable to perform the reaction of the step (A) at a temperature of −10~50° C., still more preferably 0~30° C.

Further, in the case that the reaction is carried out for less than 1 hour, amounts of the unreacted materials may increase, while, in the case that the reaction is carried out for 3 hours or more, the product may change color. Thus, the reaction time is preferably 1~3 hours.

The tocopherol dichlorophosphate obtained through filtration of reaction solution is used for the next step.

(B) reacting tocopherol dichlorophosphate represented by formula (II) with 3-aminopropane in an organic solvent, in the presence of an organic base;

In step (B), the reaction between tocopherol dichlorophosphate and 3-aminopropanol is carried out at a temperature of −10~30° C., in an equivalent ratio 1:1~1.3, in organic solvent in the presence of organic base. The above reaction produces 2-tocopherol-tetrahydro-2H-1,3,2-oxazaphosphorin P-Oxide represented by formula (III). If the mole ratio of 3-aminopropanol to tocopherol dichlorophosphate (II) is lower than 1.0, the yield of the step (B) reaction decreases. In contrast, the by-product increase if the ratio is larger than 1.3. Thus, the ratio of tocopherol dichlorophosphate to 3-aminopropanol is preferably 1:1~1.3.

Further, the reaction rate may be slow at a temperature of −10° C. or less, and the production of by-products is increased at 30° C. or more. Thus, the reaction is preferably carried out at a temperature of −10~30° C., more preferably 0~15° C.

In addition, the organic solvent and organic base employed in this step is the same as those of the step (A).

(C) filtrating the 2-tocopherol-tetrahydro-2H-1,3,2-oxazaphosphorin P-oxide, and then adjusting the pH of the filtrate to 1~5, thereafter reacting the results for hydrolysis at a temperature of 5~100° C., for 1~10 hours.

In the method according to the present invention, the filtrate of the reaction solution is concentrated under reduced pressure, thereafter the obtained residue may be hydrolyzed by using acid catalysts such as hydrochloric acid and sulfuric acid for adjusting hydrolysis conditions. Thus, the P-N bond can be hydrolyzed through adjusting pH to 1~5, preferably 2~4 by the addition of acidic solution to 2-tocopherol-tetrahydro-2H-1,3,2-oxazaphosporin P-oxide (III) solution, thereafter maintaining in a temperature of 5~100° C., and stirring. Thus, 2-tocopherol-tetrahydro-2H-1,3,2-oxazaphosporin P-oxide can be hydrolyzed through filtrating its solution, concentrating the filtrate, adjusting the pH of the residue by adding an acidic solution, and thereafter reacting the results at a temperature of 5~100° C., preferably 10~40° C., for 1~10 hours, preferably for about 2 hours. The reaction rate decreases when the reaction is carried out at a temperature of 5° C. or less, while its P—O bond gets broken at a temperature of 100° C. or more. Further, the hydrolysis is not completed when the reaction time is carried out for less than 1 hour, while P—O bond is broken at reaction times of more than 10 hours.

(D) extracting the tocopherol derivatives with organic solvent and purifying them;

Tocopherol derivatives are produced through mixing the solution obtained by the step (C) with a organic solvent, removing the impurities by washing several times with water, drying the solution with anhydrous sodium sulfate or magnesium sulfate and removing the solvent. The organic solvent employed in this step is same with those employed in step (A).

The tocopherol derivatives provided in the method of the invention can also be employed in the form of their salts obtained by neutralization with an alkali or a base. A neutralizing agent may include, but not limited thereto, salts of alkali metals including sodium and potassium; the salts of the alkali earth metals including calcium and magnesium; the salts of amine or ammonium including triethylamine.

PREFERRED EMBODIMENT OF THE INVENTION

The present invention will be described in more detail by way of the following examples. However, these examples are provided for illustration purposes only and should not be construed as limiting the scope of the invention, which is properly delineated in the accompanying claims.

PREPARATION EXAMPLE 1

(Preparation of 3-aminopropyl-α-tocopherol phosphate)

9.87 g(6.44 mmol) of phosphorus oxychloride was placed in round bottom flask and dissolved in 10 ml of tetrahydrofuran. Then, the resulting solution was cooled to 3° C., in an ice bath.

In another reactor, the mixture solution with 21.54 g(5.00 mmol) of α-tocopherol and 6.10 g(6.03 mmol) of triethylamine was diluted with 40 ml of tetrahydrofuran. Then, the solution was added dropwisely to the above solution of phosphorus oxychloride in tetrahydrofuran for about 1 hour. After adding, the mixture was stirred for about half an hour, and trimethylammonium chloride was removed through filtration. Then, the filtrate of tocopherol dichlorophosphate was cooled to 3° C. in an ice bath.

In another reactor, 3.76 g(5 mmol) of 3-amino-1-propanol and 11.11 g(10.98 mmol) of triethylamine were diluted with 20 ml of tetrahydrofuran. Then, the solution was added in drops to the above filtrate for one (1) hour to produce 2-tocopherol-tetrahydro-2H-1,3,2-oxazaphosporin P-oxide. After the addition, the mixture was stirred for half an hour. Then, the reaction solution was filtrated to remove triethylammonium chloride. The filtrate was washed with sodium chloride solution, concentrated through reduced pressure. Thereafter, 40 ml of deionized water was added to the concentrated residue, then adjusting pH to 2 by adding of hydrochloric acid. The reaction mixture was stirred at room temperature for about 2 hours, and was then washed by adding sodium chloride solution, resulting in the separation of the organic part. The organic part was dried with 10 g of anhydrous magnesium sulfate. After filtration, the solvent was removed completely, and 25 g of 3-aminopropyl-α-tocopherol phosphate was obtained in the yield of 88%.

$^1$H NMR($CDCl_3$, 300 MHz); 0.86(t, 12H), 1.00–1.80(m, 29H), 2.01(s, 3H), 2.11(s, 3H), 2.15(s, 3H), 2.40–2.50(m, 2H), 2.70–2.80(m, 2H), 3.90–4.00(m, 2H), 7.80(br, 3H)

PREPARATION EXAMPLE 2

(Preparation of 3-aminopropyl-δ-tocopherol phosphate)

23 g of 3-aminopropyl-δ-tocopherol phosphate was obtained in 87% yield, through the same method of preparation example 1 except preparing δ-tocopherol dichlorophosphate by using 20.13 g of δ-tocopherol.

$^1$H NMR($CDCl_3$, 300 MHz); 0.86(t, 12H), 1.00–1.80(m, 29H), 2.03(s, 3H), 2.55–2.65(m, 2H), 3.10–3.20(m, 2H), 4.10–4.20(m, 2H), 7.91 (br, 3H)

PREPARATION EXAMPLE 3

(Preparation of sodium salt of 3-aminopropyl-α-tocopherol phosphate)

1 g of 3-aminopropyl-α-tocopherol phosphate prepared by preparation example 1 was dissolved with 30 ml of dioxane, thereafter adjusting pH to 7 by adding 5% sodium carbonate solution. Then, through freeze-drying, sodium 3-aminopropyl-α-tocopherol phosphate was obtained as a faint yellow solid.

PREPARATION EXAMPLE 4

(Preparation of potassium salt of 3-aminopropyl-α-tocopherol phosphate)

1 g of 3-aminopropyl-α-tocopherol phosphate prepared by preparation example 1 was dissolved with 30 ml of dioxane, thereafter adjusting pH in 7 by adding potassium hydroxide. Then, through freeze-drying, potassium 3-aminopropyl-α-tocopherol phosphate was obtained as a faint yellow solid.

Experimental Example 1

Safety of Tocopherol Derivatives

If the tocopherol derivatives should be used as cosmetic ingredient, their safety in the living body is very important. The present invention thus examined whether the tocopherol derivatives of the invention have toxicity and cause irritation to the body or not. The product of Preparation Example 1 was dissolved in squalene to produce 10% of solution sample, and the sample was employed in safety experiments.

1-1. Acute oral toxicity test in mice: 1 ml/kg of the sample was administrated to total ten (10) mice (male and female were separately five (5) mice). As a result, no death of mice was observed. And the difference in the body weight after administration was also insignificant.

1-2. Acute dermal toxicity test in mice and rabbits: 0.2 ml/kg of the sample was administrated percutaneously once to a total of ten (10) mice (five male and five female). After two weeks of observation, no mice administered with the sample exhibited abnormal symptoms or changes in body weight. When the same experiment was performed on rabbits, No abnormal symptom and change of body weight were observed in rabbit administrated with the sample.

1-3. Primary skin irritation test: 0.1 ml of test sample was applied to back site (2.5 cm×2.5 cm) of each of 12 rabbits depilated 24 hours before. As a result, no skin irritation was observed.

1-4. Eye irritation test: The sample was diluted with saline to produce 2% of test sample, and 0.1 ml of the diluted solution was applied to the eye of each of nine (9) rabbits. As a result, no eye irritation on cornea, iris and conjunctiva was observed.

1-5. Skin sensitization test: Test was carried out for six (6) (three males and three females) Guinea pigs according to Maggnusson and Kligman's procedure. As a result, no skin abnormality such as erythema, edema or freckles was observed.

1-6. Human patch test: Human patch test was carried out for thirty (30) healthy women aged 20~28 according to CTFA Guideline(The Cosmetic Toiletry and Fragrance Association, INC., Washington, D.C. 20036, 1991). As a result, primary irritation response was not observed.

1-7. Repeat Insult Human Patch Test: Human patch test was carried out for subjects according to CTFA Guideline. As a result, no repeat irritation or no sensitive irritation was observed.

As mentioned in the results of the above safety experiments, the tocopherol derivatives according to the present invention are materials safe for skin application.

Experimental Example 2

Stability Test of Tocopherol Derivatives

Each 3 g of preparation example 1 product and tocopherol was dissolved with 100 ml of cetylethyl-hexanoate. While maintaining in 60° C. thermostatic bath for six (6) months, the preservation of each compound was observed. Then, residual ratio of each compound was analyzed by using HPLC. Here, phenyl column, eluate solution of 70% aqueous THF solution including 10 mM SDS and 50 mM $H_3PO_4$, flow rate of 1 ml/min and detection of 286 nm was used as HPLC analysis condition of preparation example 1. And ODS column, MeOH as eluate solution, flow rate of 1 ml/min and detection of 290 nm was used as HPLC analysis condition of tocopherol for control. The results were shown in Table 1. The coloration degree of each compound was also observed by the unaided eye. The results are shown in Table 2.

TABLE 1

| Month | | 1 | 2 | 3 | 4 | 5 | 6 |
|---|---|---|---|---|---|---|---|
| Preparation example 1 (Residual ration(%)) | 100 | 100 | 100 | 100 | 100 | 100 | 100 |
| Tocopherol (Residual ration(%)) | 100 | 100 | 97 | 92 | 88 | 82 | 76 |

TABLE 2

| Month | | 1 | 2 | 3 | 4 | 5 | 6 |
|---|---|---|---|---|---|---|---|
| Preparation example 1 | – | – | – | – | – | – | – |
| Tocopherol | – | – | – | + | + | ++ | ++ |

*coloration:
–faint yellow,
+small;
++medium;
+++large

As shown in Tables 1 and 2, tocopherol derivatives of preparation example 1 did not change in color, but tocopherol as a control increase in coloration at four (4) months or more. And quantitative analysis by NMR Spectroscopy indicated that preparation example 1 was more stable.

Experimental Example 3

Effect on Promoting Biosynthesis of Collagen

The effect on promoting biosynthesis of collagen was examined in vitro for assaying the effect of the present invention on skin, comparing to 3-amino propane phosphate.

Fibroblast cells of infant were inoculated on 24-wells($10^5$ cells/well). They were washed with PBS once. And then, preparation example 1 and 3-aminopropane phosphate as a control were treated by the concentration shown Table 3, and were incubated at $CO_2$ incubator for 24 hours. Each supernatant was collected, and the variation of procollagen was measured by using procollangen type (I) ELISA kit. The results are shown in Table 3. The value of biosynthesis activity was calculated by comparing to 100, the value of none-treated sample.

TABLE 3

| | Concentration (%) | Biosynthesis activity (%) |
|---|---|---|
| 3-aminopropane phosphate | $10^{-4}$ | 146 |
| Preparation example 1 | $10^{-6}$ | 141 |

As shown in Table 3, the tocopherol derivatives according to the present invention have excellent biosynthesis activity of collagen. Thus, when the tocopherol derivatives of the invention were applied to skin, it can be known that ageing and oxidation of bio-membrane may be prevented.

Experimental Example 4

Hydrolysis by Biological Enzyme

When applied to skin percutaneously, the tocopherol derivatives according to the present invention were assayed whether they may be hydrolyzed by biological enzyme in living body into tocopherol and 3-aminopropane phosphate. The phosphodiesterase was used as biological enzyme, and 1% aqueous solution of 1:9 mixture of preparation example 1 and Tween 20 was prepared to use as an assay sample. After the stirring mixture of the above enzyme, assay sample and medium solution at a temperature of 37° C. for 24 hours, analysis for the hydrolysis ratio of tocopherol derivatives was carried out by using HPLC(MeOH:THF=9:1, R.T.=13.695 min, tocopherol). As a result, 40% of the tocopherol derivatives of the invention were hydrolyzed by biological enzyme. However, because an amount of emulsifying agent was used for improving insolubility of compound of preparation example 1 on water, it seemed that inactivation of the biological enzyme was increased thereby. Thus, the actual hydrolysis of tocopherol derivatives by biological enzyme may be made in much larger amount.

Experimental Example 5

Measurement of Antioxidant Activity Using Lard Oil 2.0 g of Lard oil was poured on petri-dish, and here 40 mmol of each of tocopherol, preparation example 1 or tocopherol acetate was added. Then, the mixture solution was maintained in a dark room of 60° C. The oxidation ratio of Lard oil was determined by daily measurement of the change in weight. The result is shown in FIG. 1. The less is the changeability in weight of Lard oil, the stronger is the antioxidant ability, because the increase in weight of Lard oil is related to the oxidation of Lard oil.

In the meantime, when the change in weight of Lard oil was not observed any longer, the oxidation ratio was determined by using NMR spectroscopy. As a result, tocopherol and tocopherol acetate and non-treated sample had about 90% oxidation ratio. However, the Preparation Example 1 according to the invention had only about 5% oxidation ratio.

Experimental Example 6

Measurement of Antioxidant Activity Using Linoleic Acid 2.0 g of pure linoleic acid was poured on a petri-dish, and here 40 mmol of each of tocopherol, preparation example 1 or tocopherol acetate was added. Then, the mixture solution was maintained in a dark room of 60° C. The oxidation ratio of linoleic oil was measured by daily measurement of the change in weight. The result is shown in FIG. 1. The less is the changeability in weight of linoleic acid, the stronger is the antioxidant ability, because the increase in weight of linoleic acid is related to the oxidation of linoleic oil.

In the meantime, when the change in weight of linoleic acid was not observed any longer, the oxidation ratio was determined by using NMR spectroscopy. As a result, tocopherol and tocopherol acetate and non-treated sample had about 83% oxidation ratio. However, the Preparation Example 1 according to the invention had only about 3% oxidation ratio.

As shown in Experimental Examples 5 and 6, it can be known that the tocopherol derivatives of the invention have more excellent antioxidant activity than other tocopherol derivatives.

Although preferred embodiments of the present invention have been described in detail hereinabove, it should be clearly understood that many variations and/or modifications of the basic inventive concepts herein taught which may appear to those skilled in the art will still fall within the spirit and scope of the present invention as defined in the appended claims.

What is claimed is:

1. The tocopherol derivatives represented by a following general formula (I) or their salts:

(1)

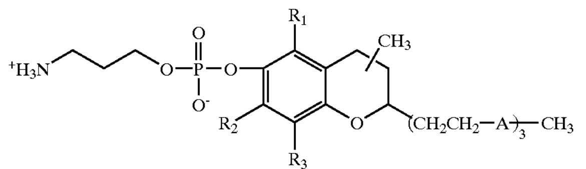

Wherein, $R_1$, $R_2$ and $R_3$ are H or methyl group, and at least one positions selected from group consisting of the $R_1$, $R_2$ and $R_3$ positions are methyl group; and, A is $CH_2$—$CH(CH_3)$— or $CH{=}C(CH_3)$—.

2. A method for preparing said tocopherol derivatives of claim 1, which comprises the following:

(A) reacting tocopherol with phosphorous oxychloride at a temperature of −10~50° C., in an equivalent ratio of 1:1~1.3, in the presence of an organic base, in an organic solvent to produce tocopherol dichlorophosphate;

(B) reacting the tocopherol dichlorophosphate produced by said (A) step with 3-aminopropanol, in the presence of an organic base, in an organic solvent to produce 2-tocopherol-tetrahydro-2H-1,3,2-oxazaphosphorin P-Oxide;

(C) filtering the solution containing 2-tocopherol-tetrahydro-2H-1,3,2-oxazaphosphorin P-Oxide produced by said step (B), adjusting pH of filtrate to 1~5, and then hydrolyzing the solution at a temperature of 5~100° C., for 1~10 hours; and, (D) extracting tocopherol derivatives in the presence of organic solvent and purifying them.

3. The method according to claim 2, wherein said organic solvent employed in said steps (A), (B) or (D) is selected from a group consisting of dichloromethane, tetrahydrofuran, ethyl acetate, chloroform and ethyl ether.

4. The method according to claim 2, wherein said organic base employed in said steps (A) or (B) is pyridine or triethylamine.

* * * * *